United States Patent
Rickey et al.

(10) Patent No.: US 6,290,983 B1
(45) Date of Patent: *Sep. 18, 2001

(54) PREPARATION OF BIODEGRADABLE, BIOCOMPATIBLE MICROPARTICLES CONTAINING A BIOLOGICALLY ACTIVE AGENT

(75) Inventors: Michael E. Rickey, Loveland; J. Michael Ramstack, Lebanon, both of OH (US); Danny H. Lewis, Hartselle, AL (US)

(73) Assignee: Alkermes Controlled Therapeutics Inc. II., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/578,717

(22) Filed: May 26, 2000

Related U.S. Application Data

(63) Continuation of application No. 09/263,098, filed on Mar. 5, 1999, now Pat. No. 6,110,503, which is a continuation of application No. 09/071,865, filed on May 4, 1998, now Pat. No. 5,916,598, which is a continuation of application No. 08/850,679, filed on May 2, 1997, now Pat. No. 5,792,477.
(60) Provisional application No. 60/041,551, filed on May 7, 1996.

(51) Int. Cl.[7] .................. A61F 2/00; A61K 9/14

(52) U.S. Cl. ............... 424/426; 424/489; 424/486

(58) Field of Search .................... 424/501, 502, 424/426, 489, 486

(56) References Cited

U.S. PATENT DOCUMENTS

| | | |
|---|---|---|
| 3,523,906 | 8/1970 | Vrancken et al. . |
| 3,691,090 | 9/1972 | Kitajima et al. . |
| 3,737,337 | 6/1973 | Schnoring et al. . |
| 3,773,919 | 11/1973 | Boswell et al. . |
| 3,891,570 | 6/1975 | Fukushima et al. . |

(List continued on next page.)

FOREIGN PATENT DOCUMENTS

| | | |
|---|---|---|
| 0 486 959 A1 | 5/1992 | (EP) . |
| WP 90/03678 | 5/1989 | (WO) . |
| WO 90/13361 | 11/1990 | (WO) . |
| WO 94/10982 | 5/1994 | (WO) . |
| WO 95/13799 | 5/1995 | (WO) . |

OTHER PUBLICATIONS

Koch Engineering Co., Inc., Static Mixing Technology advertisement, pp. 1–15.

Baker, J.R., "Motionless Mixers Stir Up New Uses," *Chemical Engineering Progress*, pp. 32–38 (Jun. 1991).

Mutsakis, M., et al., "Advances in Static Mixing Technology," *Chemical Engineering Progress*, pp. 42–48 (Jul. 1986).

Bodmeier, R., et al., International Journal of Pharmaceutics, 43:179–186 (1988).

Beck, L.R., et al., Biology of Reproduction, 28:186–195 (Feb. 1983).

(List continued on next page.)

Primary Examiner—Thurman K. Page
Assistant Examiner—Robert M. Joynes
(74) Attorney, Agent, or Firm—Andrea G. Reister; Covington & Burling

(57) ABSTRACT

A method for preparing biodegradable, biocompatible microparticles. A first phase is prepared that includes a biodegradable, biocompatible polymer, an active agent, and a solvent. A second phase is prepared. The first and second phases are combined to form an emulsion in which the first phase is discontinuous and the second phase is continuous. The discontinuous first phase is separated from the continuous second phase. The residual level of solvent in the discontinuous first phase is reduced to less than about 2% by weight.

10 Claims, 4 Drawing Sheets

U.S. PATENT DOCUMENTS

| | | |
|---|---|---|
| 3,960,757 | 6/1976 | Morishita et al. . |
| 4,221,862 | 9/1980 | Naito et al. . |
| 4,384,975 | 5/1983 | Fong . |
| 4,389,330 | 6/1983 | Tice et al. . |
| 4,530,840 | 7/1985 | Tice et al. . |
| 4,940,588 | 7/1990 | Sparks et al. . |
| 5,066,436 | 11/1991 | Komen et al. . |
| 5,407,609 | 4/1995 | Tice et al. . |
| 5,478,564 | 12/1995 | Wantier et al. . |
| 5,541,172 | 7/1996 | Labric et al. . |
| 5,650,173 | 7/1997 | Ramstack et al. . |
| 5,654,008 | 8/1997 | Herbert et al. . |
| 5,688,801 | 11/1997 | Mesens et al. . |
| 5,792,477 | 8/1998 | Rickey et al. . |
| 5,916,598 | 8/1998 | Rickey et al. . |
| 5,945,126 | 8/1999 | Thanoo et al. . |
| 6,110,503 * | 8/2000 | Rickey et al. .................... 424/501 |

OTHER PUBLICATIONS

Toyomi Sato et al., Pharmaceutical Research, 5:21–30 (1988).

Wen–I Li et al., Journal of Controlled Release, 37:199–214 (Dec. 1995).

H.V. Maulding et al., Journal of Controlled Release, 3:103–117 (Mar. 1986).

Hongkee Sah et al., Pharmaceutical Research, 13:360–367 (Mar. 1996).

R. Jalil et al., Journal of Microencapsulation, vol. 7, No. 3, Jul.–Sep. 1990, pp. 297–319.

B. Conti et al., "Use of polylactic acid for the preparation of microparticulate drug delivery systems," XP 000259942, Journal of Microencapsulation, 9 (1992) Apr./Jun., No. 2, Lond GB, pp. 153–166.

Maa, Y.F. et al., "Liquid–liquid emulsification by static mixers for use in Microencapsulation." XP 000589904, Journal of Microencapsulation, 13 (1996), No. 4, pp. 419–433.

* cited by examiner

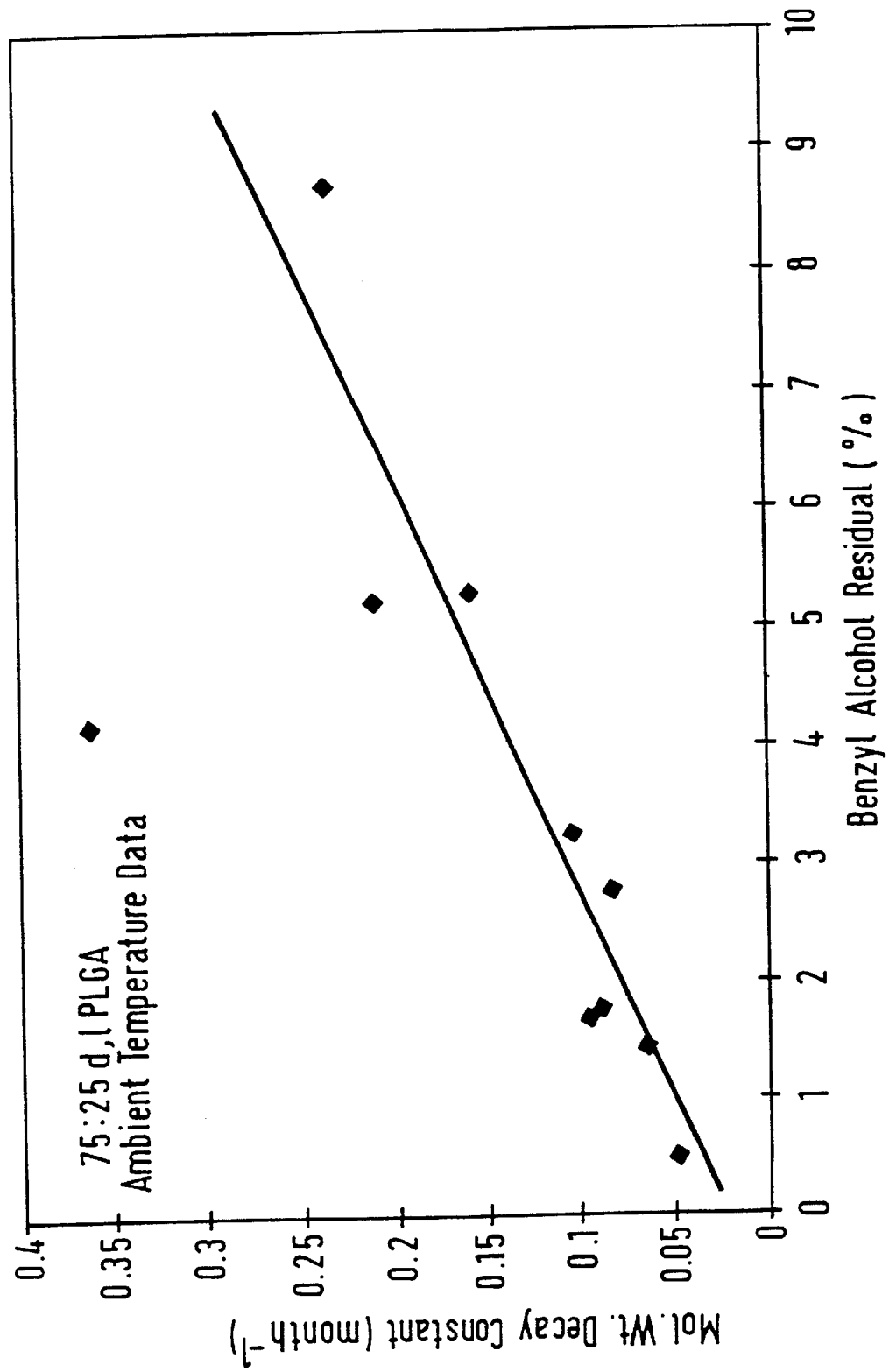

PREPARATION OF BIODEGRADABLE, BIOCOMPATIBLE MICROPARTICLES CONTAINING A BIOLOGICALLY ACTIVE AGENT

This application is a continuation of application Ser. No. 09/263,098, filed Mar. 5, 1999, now U.S. Pat. No. 6,110,503, which is a continuation of application Ser. No. 09/071,865, filed May 4, 1998 now U.S. Pat. No. 5,916,598 which is a continuation of application Ser. No. 08/850,679, filed May 2, 1997 now U.S. Pat. No. 5,792,477 which claims priority to provisional application Ser. No. 60/041,551, filed May 7, 1996, the entirety of which is hereby incorporated by reference.

BACKGROUND OF THE INVENTION

1. Field of the Invention

This invention relates to microparticles having a reduced level of residual solvent(s) and to a method for the preparation of such microparticles. More particularly, the present invention relates to pharmaceutical compositions comprising controlled-release microparticles having improved shelf-life, said microparticles comprising active agents encapsulated within a polymeric matrix, and to a method for forming such microparticles.

2. Description of the Related Art

Compounds can be encapsulated in the form of microparticles by a variety of known methods. It is particularly advantageous to encapsulate a biologically active or pharmaceutically active agent within a biocompatible, biodegradable, wall-forming material (e.g., a polymer) to provide sustained or delayed release of drugs or other active agents. In these methods, the material to be encapsulated (drugs or other active agents) is generally dissolved, dispersed, or emulsified, using known mixing techniques, in a solvent containing the wall-forming material. Solvent is then removed from the microparticles and thereafter the microparticle product is obtained.

An example of a conventional microencapsulation process is disclosed in U.S. Pat. No. 3,737,337 wherein a solution of a wall or shell forming polymeric material in a solvent is prepared The solvent is only partially miscible in water. A solid or core material is dissolved or dispersed in the polymer-containing solution and, thereafter, the core-material-containing solution is dispersed in an aqueous liquid that is immiscible in the organic solvent in order to remove solvent from the microparticles.

Another example of a process in which solvent is removed from microparticles containing a substance is disclosed in U.S. Pat. No. 3,523,906. In this process, a material to be encapsulated is emulsified in a solution of a polymeric material in a solvent that is immiscible in water and then the emulsion is emulsified in an aqueous solution containing a hydrophilic colloid. Solvent removal from the microparticles is then accomplished by evaporation and the product is obtained.

In still another process, as disclosed in U.S. Pat. No. 3,691,090, organic solvent is evaporated from a dispersion of microparticles in an aqueous medium, preferably under reduced pressure.

Similarly, U.S. Pat. No. 3,891,570 discloses a method in which microparticles are prepared by dissolving or dispersing a core material in a solution of a wall material dissolved in a solvent having a dielectric constant of 10 or less and poor miscibility with a polyhydric alcohol then emulsifying in fine droplets through dispersion or solution into the polyhydric alcohol and finally evaporating the solvent by the application of heat or by subjecting the microparticles to reduced pressure.

Another example of a process in which an active agent may be encapsulated is disclosed in U.S. Pat. No. 3,960,757. Encapsulated medicaments are prepared by dissolving a wall material for capsules in at least one organic solvent, poorly miscible with water, that has a boiling point of less than 100° C., a vapor pressure higher than that of water, and a dielectric constant of less than about 10; dissolving or dispersing a medicament that is insoluble or slightly soluble in water in the resulting solution; dispersing the resulting solution or dispersion to the form of fine drops in a liquid vehicle comprising an aqueous solution of a hydrophilic colloid or a surface active agent, and then removing the organic solvent by evaporation.

Tice et al in U.S. Pat. No. 4,389,330 describe the preparation of microparticles containing an active agent by using a two-step solvent removal process. In the Tice et al. process, the active agent and the polymer are dissolved in a solvent The mixture of ingredients in the solvent is then emulsified in a continuous-phase processing medium that is immiscible with the solvent A dispersion of microparticles containing the indicated ingredients is formed in the continuous-phase medium by mechanical agitation of the mixed materials. From this dispersion, the organic solvent can be partially removed in the first step of the solvent removal process. After the first stage, the dispersed microparticles are isolated from the continuous-phase processing medium by any convenient means of separation. Following the isolation, the remainder of the solvent in the microparticles is removed by extraction. After the remainder of the solvent has been removed from the microparticles, they are dried by exposure to air or by other conventional drying techniques.

Tice et al., in U.S. Pat. No. 4,530,840, describe the preparation of microparticles containing an anti-inflammatory active agent by a method comprising: (a) dissolving or dispersing an anti-inflammatory agent in a solvent and dissolving a biocompatible and biodegradable wall forming material in that solvent; (b) dispersing the solvent containing the anti-inflammatory agent and wall forming material in a continuous-phase processing medium; (c) evaporating a portion of the solvent from the dispersion of step (b), thereby forming microparticles containing the anti-inflammatory agent in the suspension; and (d) extracting the remainder of the solvent from the microparticles.

WO 90/13361 discloses a method of microencapsulating an agent to form a microencapsulated product, having the steps of dispersing an effective amount of the agent in a solvent containing a dissolved wall forming material to form a dispersion; combining the dispersion with an effective amount of a continuous process medium to form an emulsion that contains the process medium and microdroplets having the agent, the solvent, and the wall forming material; and adding the emulsion rapidly to an effective amount of an extraction medium to extract the solvent from the microdroplets to form the microencapsulated product Bodmeier, R., et al., *Interational Journal of Pharmaceutics* 43:179–186 (1988), disclose the preparation of microparticles containing quinidine or quinidine sulfate as the active agent and poly(D,L-lactide) as the binder using a variety of solvents including methylene chloride, chloroform, and benzene as well as mixtures of methylene chloride and a water miscible liquid, such as acetone, ethyl acetate, methanol, dimethylsulfoxide, chloroform, or benzene to enhance drug content.

Beck, L. R., et al., *Biology of Reproduction* 28:186–195 (1983), disclose a process for encapsulating norethisterone in a copolymer of D,L-lactide and glycolide by dissolving both the copolymer and the norethisterone in a mixture of chloroform and acetone that is added to a stirred cold aqueous solution of polyvinyl alcohol to form an emulsion and the volatile solvents removed under reduced pressure to yield microcapsules.

Kino et al., in WO 94/10982, disclose sustained-release microspheres consisting of a hydrophobic antipsychotic agent encapsulated in a biodegradable, biocompatible high polymer. The antipsychotic may be fluphenazine, chlorpromazine, sulpiride, carpipramine, clocapramine, mosapramine, risperidone, clozapine, olanzapine, sertindole, or (pref.) haloperidol or bromperidol. The biodegradable, biocompatible high polymer may be a fatty acid ester (co)polymer, polyacrylic acid ester, polyhydroxylactic acid, polyallylene oxalate, polyorthoester, polycarbonate or polyamino acid. The polymer or copolymer of a fatty acid ester can be polylactic acid, polyglycolic acid, polycitric acid, polymalic acid, or lactic/glycolic acid copolymer. Also disclosed as being useful are poly($\alpha$-cyanoacrylic acid ester), poly($\beta$-hydroxylactic acid), poly(tetramethylene oxalate), poly(ethylene carbonate), poly-$\gamma$-benzyl-L-glutamic acid, and poly-L-alanine.

The antipsychotic (pref with mean particle diameter below 5 microns) is suspended in the biodegradable high polymer dissolved in an oil solvent (boiling at 120° C. or below), added to water containing an emulsifier (such as an anionic or nonionic surfactant, PVP, polyvinyl alcohol, CMC, lecithin or gelatine), emulsified and dried.

The uses and advantages are said to be: administration of the antipsychotic can be carried out by injection (e.g., subcutaneous or intramuscular) at extended intervals (e.g., every one to eight weeks); compliance during antipsychotic maintenance therapy is improved; the need for surgical implantation is avoided; and administration is carried out with negligible discomfort.

Very often the solvents used in the known microencapsulation processes are halogenated hydrocarbons, particularly chloroform or methylene chloride, which act as solvents for both the active agent and the encapsulating polymer. The presence of small, but detectable, halogenated hydrocarbon residuals in the final product, however, is undesirable, because of their general toxicity and possible carcinogenic activity.

In Ramstack et al., U.S. application Ser. No. 08/298,787 (now U.S. Pat. No. 5,650,173), the entirety of which is incorporated herein by reference, a process was disclosed for preparing biodegradable, biocompatible microparticles comprising a biodegradable, biocompatible polymeric binder and a biologically active agent, wherein a blend of at least two substantially non-toxic solvents, free of halogenated hydrocarbons, was used to dissolve both the agent and the polymer. The solvent blend containing the dissolved agent and polymer was dispersed in an aqueous solution to form droplets. The resulting emulsion was then added to an aqueous extraction medium preferably containing at least one of the solvents of the blend, whereby the rate of extraction of each solvent was controlled, whereupon the biodegradable, biocompatible microparticles containing the biologically active agent were formed. The preferred active agents for encapsulation by this process were norethindrone, risperidone, and testosterone and the preferred solvent blend was one comprising benzyl alcohol and ethyl acetate.

Risperidone encapsulated in microparticles prepared using a benzyl alcohol and ethyl acetate solvent system is also described in Mesens et al., U.S. patent application 08/403,432 (now U.S. Pat. No. 5,654,008), the entirety of which is also incorporated herein by reference.

In the course of the continuing development of the aforementioned microencapsulated risperidone product with the ultimate goal of commercialization, it was discovered that the maintenance of the product integrity upon long-term storage was a problem, i.e., a degradation process was taking place. A need therefore was found to exist for a means by which the degradation rate could be reduced, thereby increasing the shelf-life of the product and enhancing its commercial feasibility.

SUMMARY OF THE INVENTION

The present inventors discovered that, by reducing the level of residual processing solvent, the rate of degradation of the product could be significantly diminished. The present inventors discovered that one degradation process resulted, at least in part, from hydrolysis of the polymeric matrix, and that the rate of hydrolysis was directly influenced by the level of residual processing solvent, i.e., benzyl alcohol, in the product. By reducing the level of residual solvent in the microparticles, the rate of degradation was reduced, thereby increasing shelf-life.

The present invention relates to an improved method of preparing a pharmaceutical composition in microparticle form designed for the controlled release of an effective amount of a drug over an extended period of time, whereby the composition exhibits increased shelf-life. The useful shelf-life can be increased to about two or more years for microparticles made in accordance with the method of the present invention. The invention also relates to the novel composition, per se, which comprises at least one active agent, at least one biocompatible, biodegradable encapsulating binder, and less than about two percent by weight residual solvent, the residual solvent being residual derived from a solvent employed in the preparation of the microparticles.

More particularly, the present invention relates to a method for preparing biodegradable, biocompatible microparticles comprising:

A) preparing a first phase comprising:
 (1) a biodegradable, biocompatible polymeric encapsulating binder, and
 (2) an active agent having limited water solubility dissolved or dispersed in a first solvent;

B) preparing an aqueous second phase;

C) combining said first phase and said second phase under the influence of mixing means to form an emulsion in which said first phase is discontinuous and said second phase is continuous;

D) separating said discontinuous first phase from said continuous second phase; and E) washing said discontinuous first phase with
 (1) water at a temperature in the range of from about 25° C. to about 40° C., or
 (2) an aqueous solution comprising water and a second solvent for residual first solvent in said first phase, thereby reducing the level of residual first solvent to less than about 2% by weight of said microparticles.

In a preferred aspect of the above-described process, a quench step is additionally performed between steps C) and D).

The aqueous second phase can be an aqueous solution of a hydrophilic colloid or a surfactant. The aqueous second phase can be water.

In another aspect, the present invention relates to a method for preparing biodegradable, biocompatible microparticles comprising: preparing a first discontinuous phase (also referred to herein as an "oil phase" or an "organic phase") containing from about 5 weight percent to about 50 weight percent solids of which from about 5 to about 95 weight percent is a solution of biodegradable, biocompatible polymeric encapsulating binder and incorporating from about 5 to about 95 weight percent, as based on polymeric binder, of an active agent in a solvent blend, the blend comprising first and second mutually miscible co-solvents, each having a solubility in water of from about 0.1 to about 25 weight percent at 20° C.; forming an emulsion containing from 1:1 to 1:10 of the first phase in an emulsion process medium to form microdroplets of the discontinuous first phase composition in a continuous or "aqueous" second phase processing medium; adding the combined first and second phases to an aqueous extraction quench liquid at a level of from about 0.1 to about 20 liters of aqueous quench liquid per gram of polymer and active agent, the quench liquid containing the more water soluble co-solvent of the blend at a level of from about 20% to about 70% of the saturation level of the more water soluble co-solvent in the quench liquid at the temperature being used; recovering microparticles from the quench liquid; and washing the discontinuous first phase with water at an elevated temperature (i.e., above room temperature) or with an aqueous solution comprising water and a solvent for residual solvent in the first phase, thereby reducing the level of residual solvent in the microparticles. The level of residual solvent in the microparticles is preferably reduced to about 2% by weight of the microparticles.

In another aspect, the present invention relates to a method for preparing biodegradable, biocompatible microparticles comprising:

A) preparing a first phase comprising
1) a biodegradable, biocompatible polymeric encapsulating binder selected from the group consisting of poly(glycolic acid), poly-d,l-lactic acid, poly-l-lactic acid, and copolymers of the foregoing, and
2) an active agent selected from the group consisting of risperidone and 9-hydroxy risperidone, dissolved or dispersed in a blend comprising ethyl acetate and benzyl alcohol, said blend being free from halogenated hydrocarbons;

B) preparing a second phase comprising polyvinyl alcohol dissolved in water,

C) combining said first phase and said second phase in a static mixer to form an emulsion in which said first phase is discontinuous and said second phase is continuous;

D) immersing said first and said second phases in a quench liquid;

E) isolating said discontinuous first phase in the form of microparticles; and

F) washing said discontinuous first phase with an aqueous solution comprising water and ethanol, thereby reducing the level of benzyl alcohol to less than about 2% by weight of said microparticles.

In another aspect, the invention is directed to a method of preparing biodegradable, bicompatible microparticles comprising: preparing a first phase, said first phase comprising a biologically active agent, a biodegradable, biocompatible polymer, and a first solvent; preparing a second phase, wherein said first phase is substantially immiscible in said second phase; flowing said first phase through a static mixer at a first flow rate; flowing said second phase through said static mixer at a second flow rate so that said first phase and said second phase flow simultaneously through said static mixer thereby forming microparticles containing said active agent; isolating said microparticles; and washing said microparticles with water at an elevated temperature or with an aqueous solution comprising water and a second solvent for residual first solvent in said microparticles, thereby reducing the level of residual first solvent to less than about 2% by weight of said microparticles.

In further aspects of the invention, the first phase is prepared by: dissolving the biologically active agent in a solution of the polymer dissolved in a solvent free from halogenated hydrocarbons; preparing a dispersion comprising the active agent in the polymer solution; or preparing an emulsion comprising the active agent in the polymer solution.

In another aspect, the present invention relates to a pharmaceutical composition comprising biodegradable and biocompatible microparticles in a pharmaceutically acceptable carrier. The microparticles comprise a polymeric encapsulating binder having dispersed or dissolved therein an active agent, and less than about 2% by weight residual solvent, wherein the residual solvent is residual derived from a solvent employed in the preparation of the microparticles.

In another aspect, the present invention relates to a pharmaceutical composition comprising biodegradable and biocompatible microparticles, ranging in size from about 25 to about 180 microns, in a pharmaceutically acceptable carrier. The microparticles comprise a copolymer of poly (glycolic acid) and poly(d,l-lactic acid) wherein the molar ratio of lactide to glycolide is in the range of from about 85:15 to about 50:50 and having dispersed or dissolved therein from about 35 to about 40% of an active agent comprising risperidone or 9-hydroxy-risperidone, and from about 0.5 to about 1.5% by weight of benzyl alcohol.

In yet another aspect, the invention provides a method for preparing biodegradable, biocompatible microparticles that comprises contacting microparticles comprising a biodegradable, biocompatible polymer matrix containing an active agent and an organic solvent with an aqueous washing system to thereby reduce the level of residual organic solvent to less than about 2% by weight of the microparticles. The aqueous washing system is: (1) at a temperature of from about 25° C. to about 40° C. for at least part of the contacting step; or (2) an aqueous solution comprising water and a water-miscible solvent for the organic solvent. The microparticles are recovered from the aqueous washing system.

In the process of the invention, the initial content of organic solvent in the microparticles will generally be above 3.5%, more generally above 4.0% of the total weight of the microparticles. Advantageously, the process will reduce this content to less than 2%, preferably to less than 1.5% and most preferably to less than 1%. The organic solvent preferably contains a hydrophobic group containing at least 5 carbons, e.g., an aryl group such as a naphthyl or more especially a phenyl group.

The organic solvent in the microparticles will generally be present as a result of a particle formation process where the microparticles have been produced from a solution of the matrix forming polymer material in the organic solvent or in a solvent mixture or blend containing the organic solvent.

The organic solvent will preferably be a non-halogenated solvent. More preferably, the organic solvent will be an at least partially water-miscible solvent, such as an alcohol (e.g., benzyl alcohol), a linear or cyclic ether, a ketone or an ester (e.g., ethyl acetate).

Where used, a co-solvent in the solvent mixture or blend likewise will preferably be a non-halogenated solvent and particularly preferably will be an at least partially water-miscible solvent such as an alcohol (e.g., a $C_{1-4}$ alkanol such as ethanol), a linear or cyclic ether, a ketone or an ester.

The contacting with the aqueous washing system may be effected in one or more stages, e.g., a single contact or a series of washes, optionally with differently constituted aqueous washing systems. Preferably, the total contact time is for a period of ten minutes to several hours, e.g., 1 to 48 hours.

The matrix forming polymer material should of course have sufficiently limited solubility in the aqueous washing system used that the particles do not dissolve completely in the washing system during the contact period.

The process of the present invention may be carried out using pre-formed microparticles or, more preferably, may additionally comprise the production of the microparticles, conveniently using a liquid phase containing as a solvent or co-solvent the organic solvent referred to above, as well as the matrix forming polymer and the active agent. Particle formation may then be effected, for example, by spray drying or, more preferably, by forming an emulsion using a second liquid phase, e.g., an aqueous phase, with the first liquid phase being discontinuous and the second being continuous as described above.

Viewed from a further aspect, the invention provides the use of microparticles prepared by the process of the invention for the manufacture of a medicament for use in a method of diagnosis or therapy.

Viewed from a yet still further aspect, the invention provides a method of treatment of the human or non-human (e.g., mammalian) body comprising the administration thereto of a composition according to the invention.

ADVANTAGES OF THE INVENTION

Advantages of the method of the present invention are that it provides, inter alia, a biodegradable, biocompatible system that can be injected into a patient, the ability to mix microparticles containing different drugs, microparticles free from halogenated hydrocarbon residues, the ability to program release (multiphasic release patterns) to give faster or slower rates of drug release as needed, and improved shelf-life stability resulting from lowered residual solvent in the finished product.

An advantage of the products prepared by the method of the present invention is that durations of action ranging from 14 to more than 200 days can be obtained, depending upon the type of microparticle selected. In preferred embodiments, the microparticles are designed to afford treatment to patients during duration of action periods of 30 to 60 days and 60 to 100 days. A 90 day duration of action period is considered to be particularly advantageous. The duration of action can be controlled by manipulation of the polymer composition, polymer:drug ratio, microparticle size, and concentration of residual solvent remaining in the microparticle after treatment.

Another important advantage of the microparticles prepared by the process of the present invention is that practically all of the active agent is delivered to the patient because the polymer used in the method of the present invention is biodegradable, thereby permitting all of the entrapped active agent to be released into the patient.

Still another important advantage of the microparticles prepared by the process of the present invention is that residual solvent(s) in the finished microparticle can be reduced by approximately an order of magnitude whereby the useful shelf-life of the product can be increased from about six months for product made without the washing step of the present invention to about two or more years for particles made with the washing step.

A further advantage of the process of the present invention is that it may prove beneficial in controlling the release characteristics of active agent in vivo or reducing an undesirable or possibly harmful solvent.

BRIEF DESCRIPTION OF THE FIGURES

FIG. 4 depicts a graph showing the effect of the level of residual solvent (benzyl alcohol) on the decay in molecular weight of the polymeric matrix.

DETAILED DESCRIPTION OF THE PREFERRED EMBODIMENTS

Figure 1:
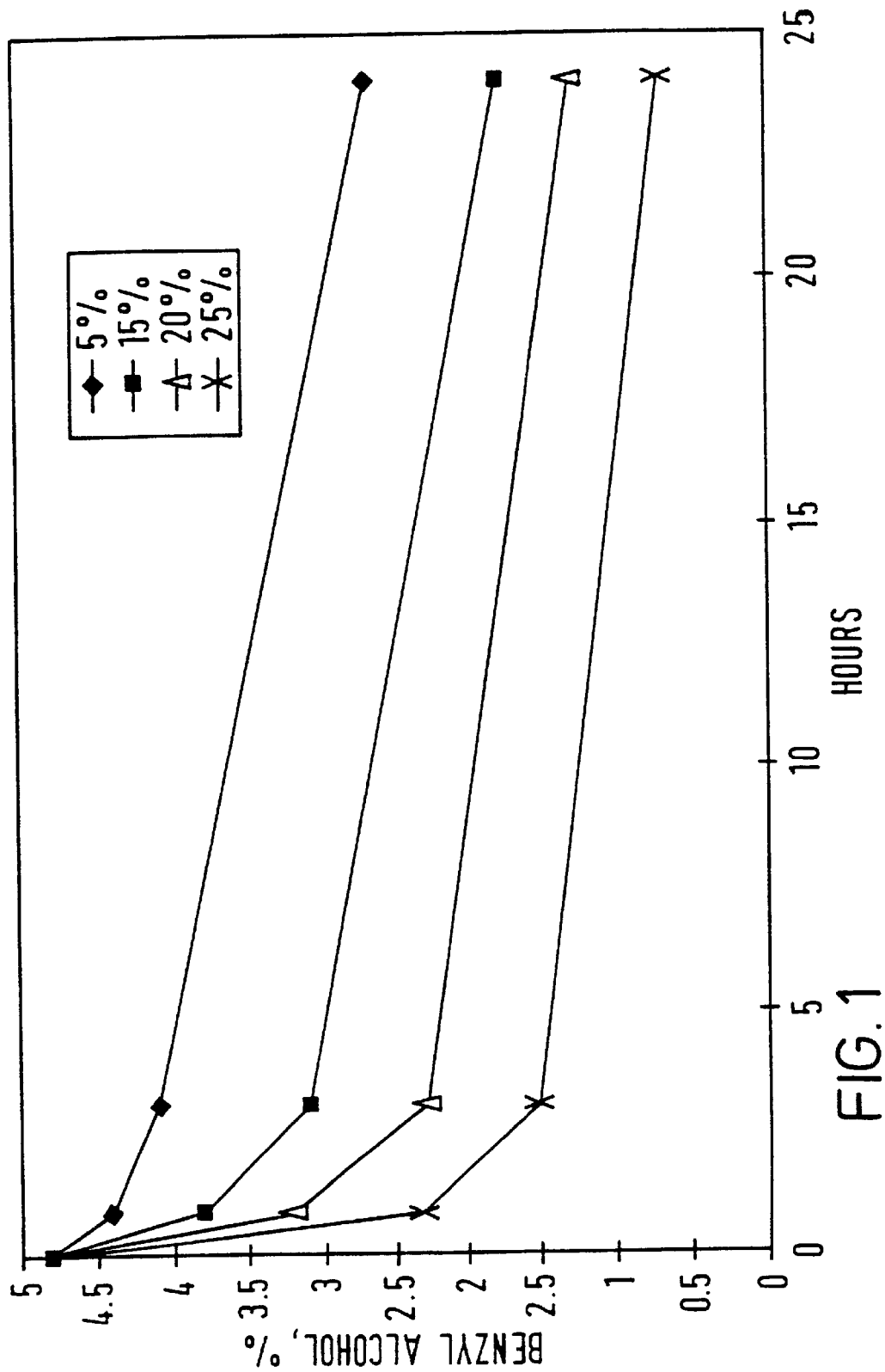
FIG. 1 depicts a graph showing the reduction in benzyl alcohol levels in the finished product as a function of ethanol concentration (5%; 15%; 20%; 25%) in an ethanol:water wash.

To ensure clarity of the description that follows, the following definitions are provided. By "microparticles" or "microspheres" is meant solid particles that contain an active agent dispersed or dissolved within a biodegradable, biocompatible polymer that serves as the matrix of the particle. By "limited water solubility" is meant having a solubility in water in the range of from about 0.1 to about 25 wt. % at 20° C. By "halogenated hydrocarbons" is meant halogenated organic solvents, i.e., $C_1$–$C_4$ halogenated alkanes, e.g., methylene chloride, chloroform, methyl chloride, carbon tetrachloride, ethylene dichloride, ethylene chloride, 2,2,2-trichloroethane, and the like. By "biodegradable" is meant a material that should degrade by bodily processes to products readily disposable by the body and should not accumulate in the body. The products of the biodegration should also be biocompatible with the body. By "biocompatible" is meant not toxic to the human body, is pharmaceutically acceptable, is not carcinogenic, and does not significantly induce inflammation in body tissues. By "weight %" or "% by weight" is meant parts by weight per total weight of microparticle. For example, 10 wt. % agent would mean 10 parts agent by weight and 90 parts polymer by weight.

In the process of the present invention, a solvent, preferably free from halogenated hydrocarbons, is used to produce biodegradable, biocompatible microparticles comprising at least one biologically active agent. A particularly preferred solvent is a solvent blend comprising at least two solvents. A first solvent component of the solvent blend is a poor solvent for the active agent, but is a good solvent for the biodegradable, biocompatible polymer used herein. A second solvent component of the solvent blend is a good solvent for the active agent. The active agent is dissolved or dispersed in the solvent. Polymer matrix material is added to the agent-containing medium in an amount relative to the active agent that provides a product having the desired loading of active agent. Optionally, all of the ingredients of the microparticle product can be blended in the solvent blend medium together.

The preferred solvent system is a blend of at least two solvents. The solvents in the solvent blend are preferably:
(1) mutually miscible with one another,
(2) capable, when blended, of dissolving or dispersing the active agent,
(3) capable, when blended, of dissolving polymeric matrix material,
(4) chemically inert to the active agent,
(5) biocompatible,
(6) substantially immiscible with any quench liquid employed, i.e., having a solubility from about 0.1 to 25%, and
(7) solvents other than halogenated hydrocarbons.

An ideal solvent blend for encapsulation of an active agent should have a high solubility for the polymeric encapsulating agent of generally at least about 5 weight percent and, preferably, at least about 20 weight percent at 20° C. The upper limit of solubility is not critical, but if over about 50 weight percent of the solution is encapsulating polymer, the solution may become too viscous to handle effectively and conveniently. This is, of course, dependent on the nature of the encapsulating polymer and its molecular weight.

The solvent system, although substantially immiscible with the continuous phase process medium and any quenching liquid, which usually are water or water-based, preferably has a limited solubility therein. If the solvent system were infinitely soluble in the process medium, microparticles would be unable to form during the emulsion phase; if the solubility of the solvent system in an extractive quenching medium were too low, however, large quantities of quenching medium would be needed. Generally, solvent solubilities of from about 0.1 to about 25% in the process medium and any quench medium are acceptable for use herein. It will often be advantageous for the quench medium, if employed, to contain from about 70 to about 20 weight percent of the saturation point of the first solvent, i.e., the solvent of higher solubility in the quench medium, to control the rate of loss of the first solvent from the microparticles into the quench medium.

Added considerations in choosing a component of the solvent blend of the present invention include boiling point (i.e., the ease with which the solvents can be evaporated, if desired to form finished product) and specific gravity (tendency of the discontinuous or oil phase to float during emulsifying and quenching). Finally, the solvent system should have low toxicity.

Generally, the solvent blend composition of two components will contain from about 25 to about 75 weight percent of the first solvent, and, correspondingly, from about 75 to about 25 weight percent of the second solvent Experiments using benzyl alcohol alone as the solvent did result in control of microparticle size as determined by inspection of the quench tank contents by optical microscopy. Upon drying, however, generally poor quality was found to have resulted. Often, recovery was difficult because of stickiness. Also, solvent residuals tended to be elevated. Using a solvent system of ethyl acetate and benzyl alcohol for the discontinuous or oil phase improved the microparticle quality and release characteristics.

The solvent blend of the present invention is preferably a blend of at least two of the following: an ester, an alcohol, and a ketone. Preferred esters are of the structure $R^1COOR^2$ where $R^1$ and $R^2$ are independently selected from the group consisting of alkyl moieties of from 1 to 4 carbon atoms, i.e., methyl, ethyl, propyl, butyl, and isomers thereof. The most preferred ester for use as one component of the solvent blend employed in the practice of the present invention is ethyl acetate.

Preferred alcohols are of the structure $R^3CH_2OH$ where $R^3$ is selected from the group consisting of hydrogen, alkyl of from 1 to 3 carbon atoms, and aryl of from 6 to 10 carbon atoms. It is more preferred that $R^3$ be aryl. The most preferred alcohol for use as one component of the solvent blend employed in the practice of the present invention is benzyl alcohol.

Preferred ketones are of the structure $R^4COR^5$ where $R^4$ is selected from the group consisting of alkyl moieties of from 1 to 4 carbon atoms, i.e., methyl, ethyl, propyl, butyl, and isomers thereof and $R^5$ is selected from the group consisting of alkyl moieties of from 2 to 4 carbon atoms, i.e., ethyl, propyl, butyl, and isomers thereof. The most preferred ketone for use as one component of the solvent blend employed in the practice of the present invention is methyl ethyl ketone.

The polymer matrix material of the microparticles prepared by the process of the present invention is biocompatible and biodegradable. The matrix material should be biodegradable in the sense that it should degrade by bodily processes to products readily disposable by the body and should not accumulate in the body. The products of the biodegradation should also be biocompatible with the body, as should any residual solvent that may remain in the microparticles.

Preferred examples of polymer matrix materials include poly(glycolic acid), poly(d,l-lactic acid), poly(l-lactic acid), copolymers of the foregoing, and the like. Various commercially available poly (lactide-co-glycolide) materials (PLGA) may be used in the method of the present invention. For example, poly (d,l-lactic-co-glycolic acid) is commercially available from Medisorb Technologies International L.P. (Cincinnati, Ohio). A suitable product commercially available from Medisorb is a 50:50 poly (d,l lactic co-glycolic acid) known as MEDISORB® 50:50 DL. This product has a mole percent composition of 50% lactide and 50% glycolide. Other suitable commercially available products are MEDISORB® 65:35 DL, 75:25 DL, 85:15 DL and poly(d,l-lactic acid) (d,l-PLA). Poly(lactide-co-glycolides) are also commercially available from Boehringer Ingelheim (Germany) under its Resomer mark. e.g., PLGA 50:50 (Resomer RG 502), PLGA 75:25 (Resomer RG 752) and d,l-PLA (Resomer RG 206), and from Birmingham Polymers (Birmingham, Ala.). These copolymers are available in a wide range of molecular weights and ratios of lactic acid to glycolic acid.

The most preferred polymer for use in the practice of this invention is the copolymer, poly(d,l-lactide-co-glycolide). It is preferred that the molar ratio of lactide to glycolide in such a copolymer be in the range of from about 85:15 to about 50:50.

It will be understood that the problem addressed by the process of the present invention is the undesirably short shelf-life engendered by the action of an active agent on the matrix polymer where the solvent, or at least one of the solvents of the solvent blend, used in making the microparticles remains in sufficient concentration in the finished product to exacerbate degrading interaction between the active agent and the polymer. This problem can be seen, for example, with an active agent having a basic moiety, such as risperidone, and a matrix polymer that has a group or linkage susceptible to base-catalyzed hydrolysis. Those skilled in the art will readily comprehend, however, that the concept of the present invention is broader than the shelf-life problem described, and is, rather, directed to the more general solution of washing products having particular tenacious solvent residuals with a wash liquid comprising water and a water miscible solvent for the tenacious solvent(s) in the product.

The molecular weight of the polymeric matrix material is of some importance. The molecular weight should be high enough to permit the formation of satisfactory polymer coatings, i.e., the polymer should be a good film former. Usually, a satisfactory molecular weight is in the range of 5,000 to 500,000 daltons, preferably about 150,000 daltons. However, since the properties of the film are also partially dependent on the particular polymeric matrix material being used, it is very difficult to specify an appropriate molecular weight range for all polymers. The molecular weight of a polymer is also important from the point of view of its influence upon the biodegradation rate of the polymer. For a diffusional mechanism of drug release, the polymer should remain intact until all of the drug is released from the microparticles and then degrade. The drug can also be released from the microparticles as the polymeric excipient bioerodes. By an appropriate selection of polymeric materials a microparticle formulation can be made in which the resulting microparticles exhibit both diffusional release and biodegradation release properties. This is useful in affording multiphasic release patterns.

Those skilled in the art will comprehend that removal of residual solvent by the wash step of the present invention may have an effect upon the drug release rate, which may be either detrimental or beneficial, depending upon the circumstances. For example, where the residual solvent is acting as a plasticizer for the matrix polymer, the glass transition temperature may be seen to decrease, thereby possibly accelerating the release rate of the active agent. If, in a given situation, a faster release rate is desirable, this result will be beneficial. If, however, the rate becomes fast enough to negatively affect the desired action of the active agent with regard to the patient, it will be incumbent upon the formulator to employ means for alleviating the accelerated release rate. Such modifications of the process, when required, are within the capability of those of ordinary skill in the relevant arts and can be realized without undue experimentation.

The formulation prepared by the process of the present invention contains an active agent dispersed in the microparticle polymetric matrix material. The amount of such agent incorporated in the microparticles usually ranges from about 1 wt. % to about 90 wt. %, preferably 30 to 50 wt. %, more preferably 35 to 40 wt. %.

In carrying out the process of the present invention, the encapsulating polymer should be essentially 100% dissolved in the solvent or solvent blend at the time the solution is emulsified. The active agent can be dispersed or dissolved in the solvent or solvent blend at the time it is added to the continuous phase process medium. The content of normally solid material (active agent plus encapsulating polymer) in the solvent blend at the time it is first emulsified should be at least 5 weight percent and preferably at least 20 weight percent. Minimizing solvent in the discontinuous or oil phase provides a better quality microparticle and requires less extraction medium.

Preferred active agents that can be encapsulated by the process of the present invention are those that comprise at least one basic moiety. Particularly preferred active agents that can be encapsulated by the process of the present invention are 1,2-benzazoles; more particularly, 3-piperidinyl-substituted 1,2-benzisoxazoles and 1,2benzisothiazoles. The most prefer active agents of this kind for treatment by the process of the present invention are 3-[2-[4-(6-fluoro-1,2-benzisoxazol-3-yl)-1-piperidinyl] ethyl]-6,7,8,9-tetrahydro-2-methyl-4H-pyrido[1,2-a] pyrimidin-4-one ("risperidone") and 3-[2-[4-(6-fluoro-1,2-benzisoxazol-3-yl)-1-piperidinyl]ethyl]-6,7,8,9-tetrahydro-9-hydroxy-2-methyl-4H-pyrido[1,2-a]pyrimidin-4-one ("9-hydroxyrisperidone") and the pharmaceutically acceptable salts thereof. Risperidone (which term, as used herein, is intended to include its pharmaceutically acceptable salts) is most preferred.

Other biologically active agents that can be incorporated using the process of the present invention include gastrointestinal therapeutic agents such as aluminum hydroxide, calcium carbonate, magnesium carbonate, sodium carbonate and the like; non-steroidal antifertility agents; parasympathomimetic agents; psychotherapeutic agents; major tranquilizers such as chlorpromazine HCl, clozapine, mesoridazine, metiapine, reserpine, thioridazine and the like; minor tranquilizers such as chlordiazepoxide, diazepam, meprobamate, temazepam and the like; rhinological decongestants; sedative-hypnotics such as codeine, phenobarbital, sodium pentobarbital, sodium secobarbital and the like; steroids such as testosterone and testosterone propionate; sulfonamides; sympathomimetic agents; vaccines; vitamins and nutrients such as the essential amino acids; essential fats and the like; antimalarials such as 4-aminoquinolines, 8-aminoquinolines, pyrimethamine and the like, anti-migraine agents such as mazindol, phentermine and the like; anti-Parkinson agents such as L-dopa; antispasmodics such as atropine, methscopolamine bromide and the like; antispasmodics and anticholinergic agents such as bile therapy, digestants, enzymes and the like; antitussives such as dextomethorphan, noscapine and the like; bronchodilators; cardiovascular agents such as anti-hypertensive compounds, Rauwolfia alkaloids, coronary vasodilarors, nitroglycerin, organic nitrates, pentaerythritotetranitrate and the like; electrolyte replacements such as potassium chloride; ergotalkaloids such as ergotamine with and without caffeine, hydrogenated ergot alkaloids, dihydroergocrte methanesulfate, dihydroergocomine methanesulfonate, dihydroergokroyptine methanesulfate and combinations thereof; alkaloids such as atropine sulfate, Belladonna, hyoscine hydrobromide and the like; analgetics; narcotics such as codeine, dihydrocodienone, meperidine, morphine and the like; non-narcotics such as salicylates, aspirin, acetaminophen, d-propoxyphene and the like; antibiotics such as the cephalosporins, chloranphenical, gentamicin, Kanamycin A, Kanamycin B, the penicillins, ampicillin, streptomycin A, antimycin A, chloropamtheniol, metromidazole, oxytetracycline penicillin G, the tetracyclines, and the like; anti-cancer agents; anticonvulsants such as mephenytoin, phenobarbital, trimethadione; anti-emetics such as thiethylperazine; antihistamines such as chlorophinazine, dimenhydrinate, diphenhydramine, perphenazine, tripelennamine and the like; anti-inflammatory agents such as hormonal agents, hydrocortisone, prednisolone, prednisone, non-hormonal agents, allopurinol, aspirin, indomethacin, phenylbutazone and the like; prostaglandins; cytotoxic drugs such as thiotepa, chlorambucil, cyclophosphamide, melphalan, nitrogen mustard, methotrexate and the like; antigens of such microorganisms as *Neisseria gonorrhea, Mycobacterium tuberculosis*, Herpes virus (humonis, types 1 and 2), *Candida albicans, Candida tropicalis, Trichomonas vaginalis, Haemophilus vaginalis*, Group B *Streptococcus ecoli, Microplasma hominis, Hemophilus ducreyi, Granu-*

*loma inguinale, Lymphopathia venereum, Treponema pallidum, Brucella abortus, Brucella melitensis, Brucella suis, Brucella canis, Campylobacter fetus, Campylobacter fetus intestinalis, Leptospira pomona, Listeria monocytogenes, Brucella ovis*, Equine herpes virus 1, Equine arteritis virus, IBR-IBP virus, BVD-MB virus, *Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinobacillus seminis, Mycoplasma bovigenitalium, Aspergillus fumigatus, Absidia ramosa, Trypanosoma equiperdum, Babesia caballi, Clostridium tetani*, and the like; antibodies that counteract the above microorganisms; and enzymes such as ribonuclease, neuramidinase, trypsin, glycogen phosphorylase, sperm lactic dehydrogenase, sperm hyaluronidase, adenosinetriphosphatase, alkaline phosphatase, alkaline phosphatase esterase, amino peptidase, trypsin, chymotrypsin, amylase, muramidase, acrosomal proteinase, diesterse, glutamic acid dehydrogenase, succinic acid dehydrogenase, beta-glycophosphatase, lipase, ATP-ase alpha-peptate gamma-glutamylotranspeptidase, sterol-3-beta-ol-dehydrogenase, and DPN-di-aprorase.

Other suitable active agents include estrogens such as diethyl stilbestrol, 17-beta-tradiol, estrone, ethinyl estradiol, mestanol, and the like; progestins such as norethindrone, norgestryl, ethynodiol diacetate, lynestrenol, medroxyprogesterone acetate, dimesthisterone, megestrol acetate, chlormadinone acetate, norgestimate, norethisterone, ethisterone, melengestrol, norethynodrel and the like; and spermicidal compounds such as nonylphenoxypolyoxyethylene glycol, benzethonium chloride, chlorindanol and the like.

Still other macromolecular bioactive agents that may be chosen for incorporation include, but are not limited to, blood clotting factors, hemopoietic factors, cytokines, interleukins, colony stimulating factors, growth factors, and analogs and fragments thereof.

The microparticles can be mixed by size or by type so as to provide for the delivery of active agent to the patient in a multiphasic manner and/or in a manner that provides different active agents to the patient at different times, or a mixture of active agents at the same time. For example, secondary antibiotics, vaccines, or any desired active agent, either in microparticle form or in conventional, unencapsulated form can be blended with a primary active agent and provided to the patient.

The mixture of ingredients in the discontinuous or oil phase solvent system is emulsified in a continuous-phase processing medium; the continuous-phase medium being such that a dispersion of microparticles containing the indicated ingredients is formed in the continuous-phase medium.

Although not absolutely necessary, it is preferred to saturate the continuous phase process medium with at least one of the solvents forming the discontinuous or oil phase solvent system. This provides a stable emulsion, preventing transport of solvent out of the microparticles prior to quenching. Similarly, a vacuum may be applied as in U.S. Pat. No. 4,389,330. Where ethyl acetate and benzyl alcohol are the components of the solvent system, the aqueous or continuous phase of the emulsion preferably contains 1 to 8 weight percent ethyl acetate and 1 to 4 weight percent benzyl alcohol.

Usually, a surfactant or a hydrophilic colloid is added to the continuous-phase processing medium to prevent the solvent microdroplets from agglomerating and to control the size of the solvent microdroplets in the emulsion Examples of compounds that can be used as surfactants or hydrophilic colloids include, but are not limited to, poly(vinyl alcohol), carboxymethyl cellulose, gelatin, poly(vinyl pyrrolidone), Tween 80, Tween 20, and the like. The concentration of surfactant or hydrophilic colloid in the process medium should be sufficient to stabilize the emulsion and will affect the final size of the microparticles. Generally the concentration of the surfactant or hydrophilic colloid in the process medium will be from about 0.1% to about 10% by weight based on the process medium, depending upon the surfactant or hydrophilic colloid, the discontinuous or oil phase solvent system, and the processing medium used. A preferred dispersing medium combination is a 0.1 to 10 wt. %, more preferably 0.5 to 2 wt. %, solution of poly(vinyl alcohol) in water.

The emulsion can be formed by mechanical agitation of the mixed phases or by adding small drops of the discontinuous phase that contains active agent and wall forming material to the continuous phase processing medium. The temperature during the formation of the emulsion is not especially critical, but can influence the size and quality of the microparticles and the solubility of the active agent in the continuous phase. Of course, it is desirable to have as little of the active agent in the continuous phase as possible. Moreover, depending upon the solvent blend and continuous-phase processing medium employed, the temperature must not be too low or the solvent and processing medium may solidify or become too viscous for practical purposes. On the other hand, it must not be so high that the processing medium will evaporate or that the liquid processing medium will not be maintained. Moreover, the temperature of the emulsion cannot be so high that the stability of the particular active agent being incorporated in the microparticles is adversely affected. Accordingly, the dispersion process can be conducted at any temperature that maintains stable operating conditions, preferably from about 20° C. to about 60° C., depending upon the active agent and excipient selected.

As stated above, in order to create microparticles containing an active agent, an organic or oil (discontinuous) phase and an aqueous phase are combined. The organic and aqueous phases are largely or substantially immiscible, with the aqueous phase constituting the continuous phase of the emulsion. The organic phase includes the active agent as well as the wall forming polymer, i.e., the polymeric matrix material. The organic phase is prepared by dissolving or dispersing the active agent(s) in the organic solvent system of the present invention. The organic phase and the aqueous phase are preferably combined under the influence of mixing means.

A preferred type of mixing means is a static mixer and a preferred method of encapsulating the active agent to form the controlled release microparticles of the present invention involves the use of such a static mixer. Preferably the combined organic and aqueous phases are pumped through a static mixer to form an emulsion and into a large volume of quench liquid, to obtain microparticles containing the active agent encapsulated in the polymeric matrix material. An especially preferred method of mixing with a static mixer in the process of the present invention is disclosed by Ramnstack et al. in U.S. application Ser. No. 08/338,305 now U.S. Pat. No. 5,654,008, the entirety of which is incorporated herein by reference.

One advantage of preparing microparticles using a static mixer is that accurate and reliable scaling from laboratory to commercial batch sizes can be done while achieving a narrow and well defined size distribution of microparticles containing biologically or pharmaceutically active agents. A further advantage of this method is that the same equipment can be used to form microparticles containing active agents of a well defined size distribution for varying batch sizes. In addition to improving process technology, static mixers are low maintenance, their small size requires less space than dynamic mixers, and they have low energy demands and comparatively low investment costs.

In practice, the organic phase and the aqueous phase are mixed in a static mixer to form an emulsion. The emulsion formed comprises microparticles containing active agent encapsulated in the polymeric matrix material. Preferably, the microparticles are then stirred in a tank containing a quench solution in order to remove most of the organic solvent from the microparticles, resulting in the formation of hardened microparticles.

Following the movement of the microparticles from the static mixer and entrance into the quench tank, the continuous-phase processing medium is diluted and much of the solvent in the microparticles is removed by extraction. In this extractive quench step, the microparticles can be suspended in the same continuous-phase processing medium used during emulsification, with or without hydrophilic colloid or surfactant, or in another liquid. The extraction medium removes a significant portion of the solvent from the microparticles, but does not dissolve them. During the extraction, the extraction medium containing dissolved solvent can, optionally, be removed and replaced with fresh extraction medium.

After the quench step has been completed, the microparticles can be isolated as stated above, and then may, if desired, be dried by exposure to air or by other conventional drying techniques, such as, vacuum drying, drying over a desiccant, or the like. This process is very efficient in encapsulating an active agent since core loadings of up to about 80 wt. %, preferably up to about 50 wt. %, can be obtained.

When a solvent blend is used to form the organic or oil phase droplets in the emulsion, one of the solvents in the solvent blend will be extracted in the quench step more quickly than the other solvent, e.g., the first solvent, ethyl acetate, in the case of the preferred ethyl acetate/benzyl alcohol blend. Thus, high residuals of the second solvent (here, benzyl alcohol) are left behind. Owing to the high boiling point of benzyl alcohol, it is not easily removed by exposure of the microparticles to air or other conventional evaporative means. To improve the efficiency of this procedure, some of the more rapidly extracted solvent can be added to the quench extraction medium prior to addition of the emulsion. The concentration of the more-rapidly-extracted solvent in the quench extraction medium generally is from about 20 to about 70% of the saturation point of the solvent in the medium at the temperature to be used for the extraction. Thus, when the emulsion is added to the quench liquid, extraction of the more rapidly extracted solvent is retarded and more of the second, more slowly extracted, solvent is removed.

The exact amount of this more-rapid-extracted solvent "spike" added to the quench liquid is of importance to final microparticle quality. Too much solvent (i.e., near the saturation point) results in porous microparticles with active agent visible on the surface, causing what may be an undesirably high rate of release. Too little solvent in the quench medium results in high residual level of the more-slowly-extracted solvent and poor microparticle quality. The temperature of the quench medium is also important as it affects solvent solubility and rate of extraction.

Both temperature and amount of solvent spike can be adjusted to contribute beneficially to the final desired product characteristics, i.e., highly porous, quick releasing microparticles, or slow releasing microparticles having a low porosity.

The quench liquid can be plain water, a water solution, or other suitable liquid, the volume, amount, and type of which depends on the solvents used in the emulsion phase. The quench liquid is preferably water. Generally, the quench liquid volume is on the order of 10 times the saturated volume (i.e., 10 times the quench volume needed to absorb completely the volume of solvent in the emulsion). Depending on the solvent system, however, quench volume can vary from about 2 to about 20 times the saturated volume. Additionally, it is convenient to describe the quench volume requirement relative to batch size (microparticle product). This ratio is an indication of efficiency of the extraction step and, in some cases, dictates the batch size for a given set of equipment The larger the ratio, the more volume is required per product weight. On the other hand, with a smaller ratio, more product can be obtained from the same amount of quench volume. This ratio can vary from about 0.1 to about 10 liters of quench volume per gram of microparticles produced. Processes with a ratio of less than about 1 liter per gram are preferred.

When using the preferred solvent combination of benzyl alcohol and ethyl acetate, the ethyl acetate content of the quench liquid appears to affect the residual solvent level in the product microparticles. At low ethyl acetate contents in the quench liquid, the benzyl alcohol residuals in the microparticles are high while ethyl acetate may be almost non-detectable. At high ethyl acetate contents in the quench liquid, more ethyl acetate may be retained by the microparticles than benzyl alcohol. At a quench volume of about 1 liter per gram of active agent and polymeric encapsulating material being quenched, about 2–4 weight percent ethyl acetate in the quench liquid is optimal at 0–10° C.

After the quenching step, the microparticles are isolated from the aqueous quench solution by any convenient means of separation—the fluid can be decanted from the microparticles or the microparticle suspension can be filtered, for example, a sieve column can be used. Various other combinations of separation techniques can be used, if desired. Filtration is preferred.

The filtered microparticles are then subjected to the washing step of the present invention in order to reduce still further the level of residual solvent(s) therein, preferably to a level in the range of from about 0.2 to about 2.0%. In practice, it has been found that, in the preferred ethyl acetate/benzyl alcohol dual solvent case, residual benzyl alcohol levels are still generally in the 4–8% range without the washing step of the present invention. This level of residual solvent in the microparticles appears to be sufficient to accelerate the degradation process, thereby reducing shelf-life. Degradation of the microparticles can occur, for example, by undesired hydrolysis of the hydrolyzable linkages of a matrix polymer by a basic active agent. Thus, the washing step(s) of the present invention are employed to reduce the residual benzyl alcohol or other solvent content in the microparticles to retard the degradation process.

As stated above, the wash solution comprises either water alone or, preferably, water and a solvent miscible therewith that is also a good solvent for the residual solvent in the microparticles. Where, as in the preferred process of the present invention, the residual solvent is benzyl alcohol, $C_1$–$C_4$ aliphatic alcohols are preferred for use in the wash solution. These alcohols are methanol, ethanol, propanol, butanol, and isomers of the foregoing. The most preferred alcohol is ethanol.

The concentration of the alcohol in the wash solution can vary depending upon the particular circumstances. Generally, the alcohol will comprise less than 50% by weight with a lower limit of about 5%. Thus, a preferred range for the alcohol concentration with normally be from about 5% to about 50% by weight. More preferably, the concentration will lie in the range of from about 15% to about 30%.

The temperature of the wash solution is also important to the efficiency of the washing step. Generally, increasing the temperature will decrease the time needed for the wash to lower the remaining residual content to the desired level. On the other hand, too high a temperature can be detrimental in that the softening temperature of the matrix polymer of the microparticles may be approached or exceeded, thereby causing clumping or stickiness. Conversely, too low a temperature may cause the matrix material to become too hard, thereby retarding the rate at which the residuals can be extracted, whereby the process may become prohibitively expensive. It has been found that a temperature range of from about 5° C. to about 40° C. is convenient and effective. Preferably, the temperature employed will bracket room temperature, i.e., from about 10° C. to about 30° C. Where water alone is used as the wash solvent, it will be employed at an elevated temperature, i.e., above room temperature, preferably in a range of from about 25° C. to about 40° C., most preferably, about 37° C.

Normally, it will be desirable to employ more than one wash step, typically two or three. After each such step, the microparticles will be separated from the wash solution by well-known separation means, e.g., filtration, decantation, centrifugation, and the like. Filtration is preferred.

After each separation step, the microparticles can, if desired, be fully or partially dried employing conventional drying means at temperatures substantially similar to those of the previous wash solution. The use of dry compressed air at temperatures ranging from about 10° C. to about 30° C. has been found especially useful and convenient and is preferred.

The microparticle product is usually made up of particles of a spherical shape, although sometimes the microparticles may be irregularly shaped. The microparticles can vary in size, ranging from submicron to millimeter diameters. Preferably, microparticles of 1–500 microns, more preferably, 25–180 microns, are prepared, whereby administration of the microparticles to a patient can be carried out with a standard gauge needle.

Preferably, the drug-loaded microparticles are dispensed to patients in a single administration, releasing the drug in a constant or pulsed manner into the patient and eliminating the need for repetitive injections.

The active agent bearing microparticles are obtained and stored as a dry material. Prior to administration to a patient, the dry microparticles can be suspended in an acceptable pharmaceutical liquid vehicle, such as, a 2.5 wt. % solution of carboxymethyl cellulose, whereupon the suspension is injected into the body.

The microparticles can be mixed by size or by type so as to provide for the delivery of active agent to the patient in a multiphasic manner and/or in a manner that provides different active agents to the patient at different times, or a mixture of active agents at the same time. For example, secondary antibiotics, vaccines, or any desired active agent, either in microparticle form or in conventional, unencapsulated form can be blended with a primary active agent and provided to the patient.

Those skilled in the art will understand that any of the numerous active agents that can be incorporated into microparticles can be prepared by the process of the present invention. Preferred active agents for use with the process of the present invention are those that contain at least one basic moiety, such as a tertiary amine group. Particularly, preferred active agents for treatment by the process of the present invention are risperidone and 9-hydroxyrisperidone and the pharmaceutically acceptable salts thereof. For those materials that have no groups detrimental to the integrity of the matrix polymer, the additional washing step(s) of the present invention may prove beneficial in ways, such as, controlling the release characteristics of active agent in vivo or reducing an undesirable or possibly harmful solvent.

The following examples further describe the materials and methods used in carrying out the invention. The examples are not intended to limit the invention in any manner.

EXAMPLE 1

In a typical 125 gram batch, 75 g of 75:25 Medisorb® lactide:glycolide copolymer and 50 g of risperidone are dissolved in 275 g of benzyl alcohol and 900.25 g of ethyl acetate as the organic phase. The aqueous phase comprises 90.0 g of polyvinyl alcohol, 8910 g of water, 646.4 g of ethyl acetate, and 298.3 g of benzyl alcohol. The organic and aqueous phases are pumped through a static mixer to form an emulsion. The resulting emulsion is passed into a quench liquid comprising 17 kg of water, 4487.8 g of ethyl acetate, 371.0 g of sodium carbonate, and 294.0 g of sodium bicarbonate. After 20 hours at approximately 10° C., the resulting microspheres are then filtered and washed with a first wash of 11.25 kg of ethanol and 33.75 kg of water for 2 hours at 10° C. The microspheres are then filtered and washed with a solution of 11.25 kg of ethanol and 33.75 kg of water for 6 hours at 25° C. A third wash of 756 g of citric acid, 482 g of sodium phosphate, and 45.0 kg of water is then applied at 25° C. for one hour to the filtered product. The product is then rinsed with water, filtered, and dried. Three batches produced according to this procedure provide risperidone contents of 37.4%, 37.0%, and 36.6% by weight. Benzyl alcohol levels were 1.36%, 1.26%, and 1.38% by weight. Ethyl acetate levels were 0.09%, 0.08%, and 0.09% by weight.

EXAMPLE 2

Effect of the Wash Process on Microparticle Characteristic

A sample of risperidone-loaded microspheres was subjected to a series of wash experiments to determine the impact on finished product characteristics and identify favorable wash conditions. The sample comprised risperidone encapsulated in a 75:25 Medisorb® lactide:glycolide copolymer. The drug content was 36.8% by weight, and the benzyl alcohol level was about 5.2% by weight prior to the washing experiments. The microspheres were transferred into the wash media, samples were withdrawn at selected time periods and vacuum dried.

FIG. 1 shows the reduction in benzyl alcohol levels in the finished product as a function of ethanol concentrations (5%; 15%; 20%; and 25%) in the ethanol:water wash. Higher ethanol levels afforded lower residual benzyl alcohol in the finished product.

Figure 2:
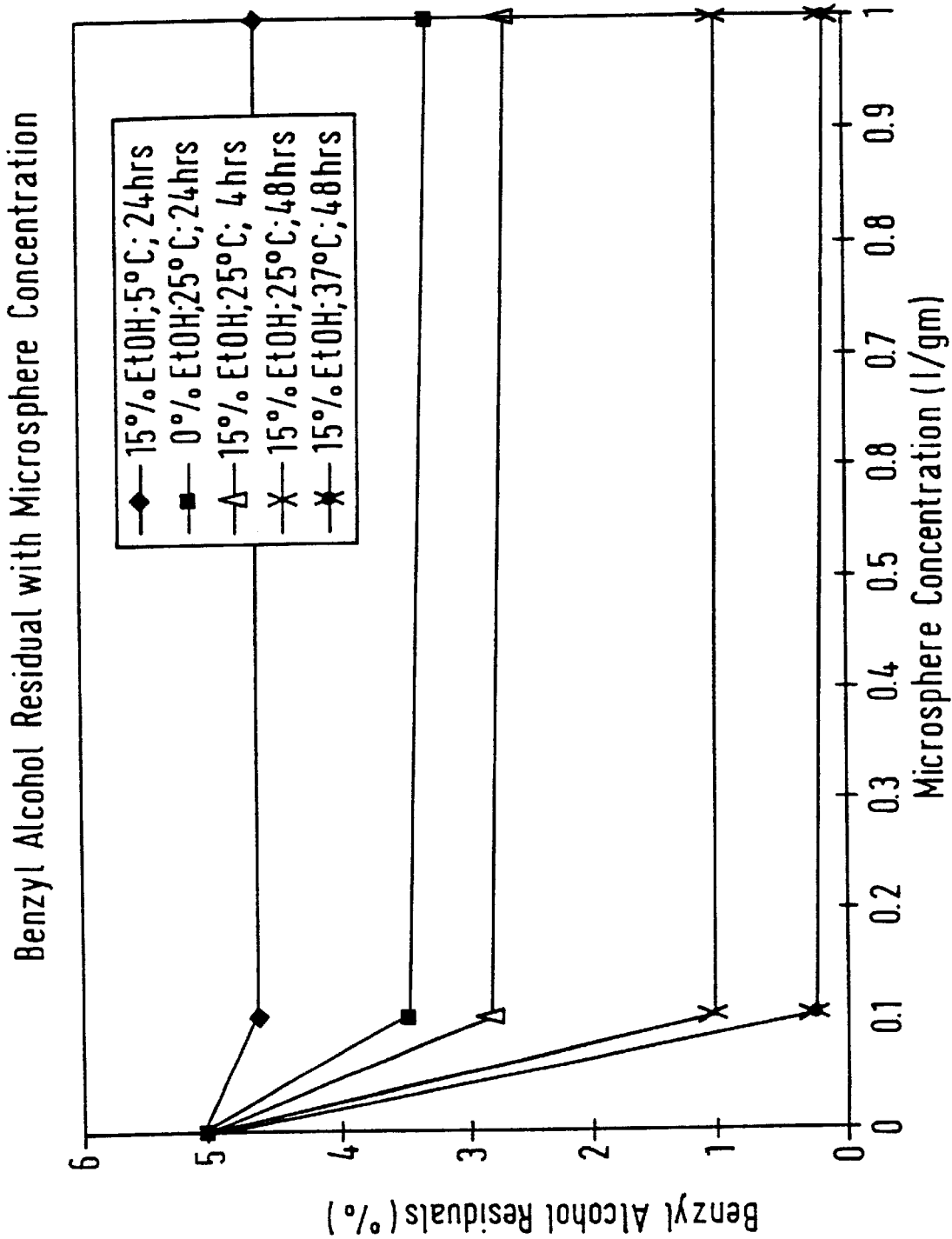
FIG. 2 depicts a graph showing the impact of microparticle concentration on the level of residual benzyl alcohol (BA) in the finished product.

FIG. 2 shows that in the range of 0.1 to 1.0 liters of solution per gram of microspheres, the concentration of microspheres in the wash step does not influence the level of residual benzyl alcohol (BA) in the finished product.

Figure 3:
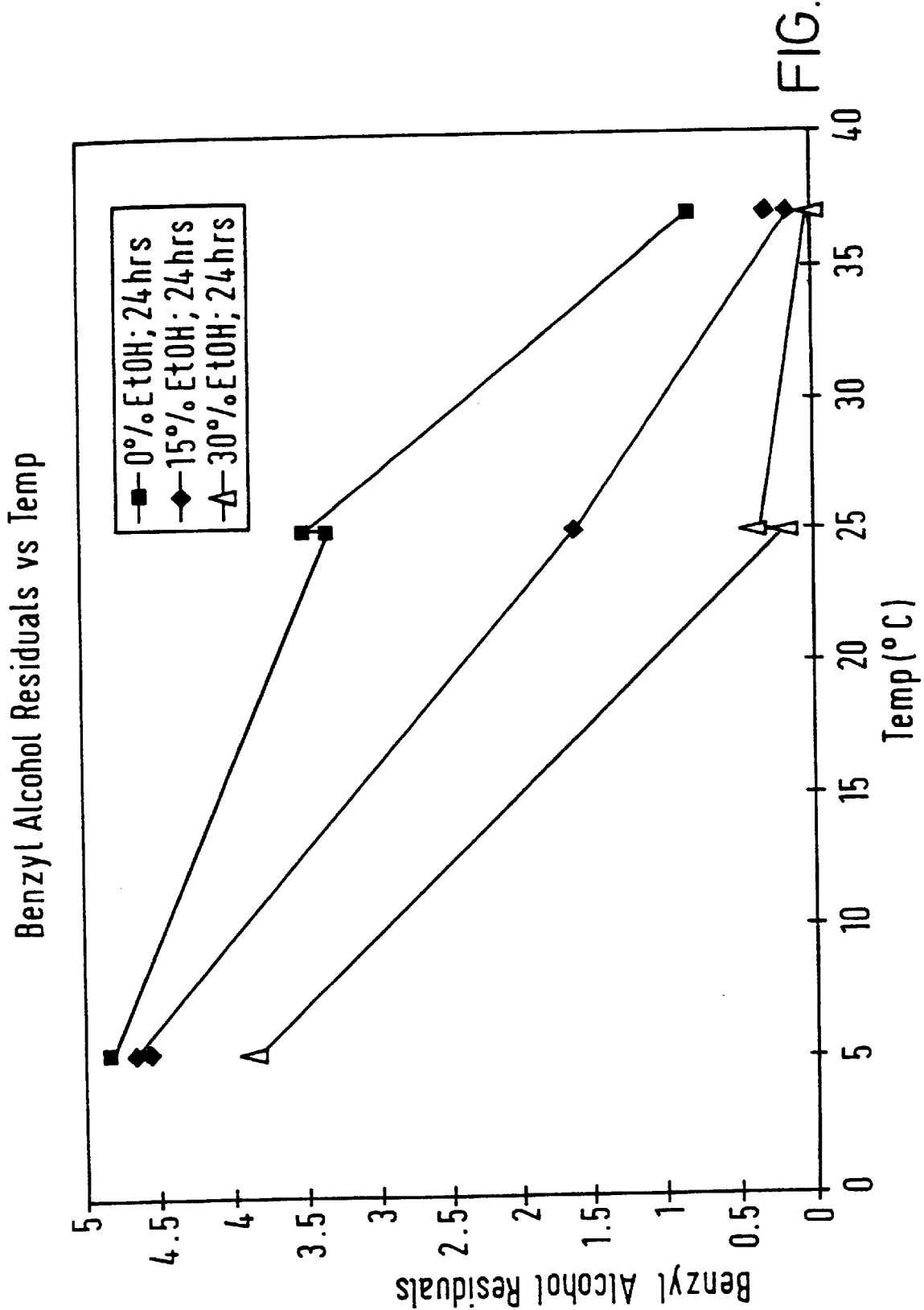
FIG. 3 depicts a graph showing the impact of temperature of the wash step on the level of residual benzyl alcohol (BA) in the finished product.

FIG. 3 shows the impact of temperature of the wash step on the level of residual benzyl alcohol in the finished product.

Table 1 shows an increase in glass-transition temperature ($T_g$) of the finished microspheres as the wash time increases, and as the concentration of ethanol increases and the corresponding concentration of benzyl alcohol decreases.

TABLE 1

Effect of Ethanol Wash Time and Concentration on Glass Transition Temperature, $T_g$

| Wash Time (Hours) | 5% Ethanol | 15% Ethanol | 20% Ethanol | 25% Ethanol |
|---|---|---|---|---|
| 0.75 | 24.2° C. | 26.5° C. | 30.1° C. | 30.8° C. |
| 3 | 26.5° C. | 26.5° C. | 32.5° C. | 35.1° C. |
| 24 | 30.9° C. | 28.7° C. | 37.3° C. | 40.1° C. |

Risperidone-loaded microspheres with various levels of benzyl alcohol were placed in stability studies at room temperature. FIG. 4 demonstrates that the degradation process as measured by the rate of hydrolysis of the biodegradable, biocompatible polymer is strongly influenced by the level of residual solvent in the finished product. The molecular weight decay constant was plotted versus residual benzyl alcohol level for ten different microsphere samples.

While various embodiments of the present invention have been described above, it should be understood that they have been presented by way of example only, and not limitation. Thus the breadth and scope of the present invention should not be limited by any of the above described exemplary embodiments, but should be defined only in accordance with the following claims and their equivalents.

What is claimed is:

1. A method for preparing microparticles, comprising:
   (A) preparing a first phase comprising a biodegradable and biocompatible polymer, a psychotherapeutic agent, and a solvent free from halogenated hydrocarbons;
   (B) preparing an aqueous phase;
   (C) combining said first phase and said aqueous phase in a static mixer to form an emulsion in which said first phase is discontinuous and said aqueous phase is continuous;
   (D) separating said discontinuous first phase from said continuous aqueous phase; and
   (E) reducing a residual level of said solvent in said discontinuous first phase to less than about 2% by weight.

2. The method of claim 1, wherein step (E) comprises:
   washing said discontinuous first phase with an aqueous solution at a temperature in the range of from about 25° C. to about 40° C.

3. The method of claim 1, wherein step (E) comprises:
   washing said discontinuous first phase with an aqueous solvent system comprising water and a second solvent for said solvent.

4. The method of claim 1, wherein said solvent is a solvent blend of at least two mutually miscible organic solvents.

5. The method of claim 1, wherein said psychotherapeutic agent comprises at least one basic moiety.

6. The method of claim 2, wherein said aqueous solution comprises water and a $C_1$–$C_4$ alcohol.

7. The method of claim 6, wherein said $C_1$–$C_4$ alcohol is ethanol.

8. The method of claim 2, wherein said aqueous solution is water.

9. The method of claim 3, wherein said aqueous solvent system further comprises a $C_1$–$C_4$ alcohol.

10. The method of claim 9, wherein said $C_1$–$C_4$ alcohol is ethanol.

* * * * *